(12) United States Patent
Niddam et al.

(10) Patent No.: US 6,930,186 B2
(45) Date of Patent: Aug. 16, 2005

(54) PROCESS FOR THE PREPARATION OF PAROXETINE SUBSTANTIALLY FREE OF ALKOXY IMPURITIES

(75) Inventors: Valerie Niddam, Yehud (IL); Ilya Avrutov, Bat Hefer (IL)

(73) Assignee: Teva Pharmacetical Industries Ltd., Petah-Tiqva (IL)

( * ) Notice: Subject to any disclaimer, the term of this patent is extended or adjusted under 35 U.S.C. 154(b) by 0 days.

(21) Appl. No.: 10/170,709

(22) Filed: Jun. 13, 2002

(65) Prior Publication Data

US 2003/0055256 A1 Mar. 20, 2003

Related U.S. Application Data

(60) Provisional application No. 60/297,881, filed on Jun. 13, 2001.

(51) Int. Cl.$^7$ .............................................. C07D 407/12
(52) U.S. Cl. ........................ 546/197; 546/198; 546/236; 546/240; 546/245
(58) Field of Search ................................ 546/197, 198, 546/236, 240, 245; 514/317, 319, 321

(56) References Cited

U.S. PATENT DOCUMENTS

| | | | |
|---|---|---|---|
| 3,912,743 A | * 10/1975 | Christensen et al. | 546/197 |
| 4,007,196 A | 2/1977 | Christensen et al. | 546/197 |
| 4,585,777 A | 4/1986 | Lassen et al. | 514/317 |
| 4,721,723 A | 1/1988 | Barnes et al. | 514/321 |
| 4,902,801 A | 2/1990 | Faruk et al. | 546/220 |
| 5,258,517 A | 11/1993 | Zepp et al. | 546/240 |
| 5,874,447 A | 2/1999 | Benneker et al. | 514/321 |
| 5,948,914 A | 9/1999 | Sugi et al. | 546/240 |
| 6,066,737 A | 5/2000 | Adger et al. | 546/240 |
| 6,080,759 A | 6/2000 | Ward et al. | 514/321 |
| 6,326,496 B1 | 12/2001 | Brennan | 546/240 |
| 2003/0004352 A1 * | 1/2003 | Brook et al. | 546/240 |

FOREIGN PATENT DOCUMENTS

EP 223334 5/1987

OTHER PUBLICATIONS

Christensen et al. "Antidepressant and Parkinsonism . . ." CA 81:552011 (1974).*
Buehler et al. "Survey of organic syhnthesis" Wiley & sons, p. 246, 253 (1970).*

* cited by examiner

Primary Examiner—Celia Chang
(74) Attorney, Agent, or Firm—Kenyon & Kenyon

(57) ABSTRACT

The present invention is directed to methods for preparing intermediates useful in the synthesis of paroxetine wherein the intermediates are substantially free of alkoxy impurities as well as to methods for preparing paroxetine and pharmaceutically acceptable salts thereof substantially free of alkoxy impurities. The alkoxy impurity is reacted with an ether cleaving agent to generate the corresponding phenol, which is separated, yielding the desired product substantially free of alkoxy impurities. Paroxetine intermediates such as PMA, paroxetine, and pharmaceutically acceptable salts thereof substantially free of alkoxy impurities also form part of the present invention.

17 Claims, 4 Drawing Sheets

PROCESS FOR THE PREPARATION OF PAROXETINE SUBSTANTIALLY FREE OF ALKOXY IMPURITIES

CROSS-REFERENCE TO RELATED APPLICATION

This application claims the benefit of provisional application Ser. No. 60/297,881, filed Jun. 13, 2001, which is incorporated herein by reference.

BACKGROUND OF THE INVENTION

Paroxetine, trans(−)-3-[(1,3-benzodioxol-5-yloxy)methyl]-4-(4-fluorophenyl) piperidine, is a serotonin (5-hydroxy-tryptamine; 5-HT) re-uptake inhibitor, having the formula (I):

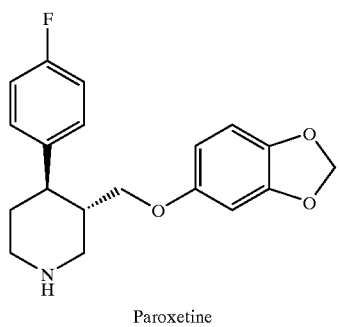

Paroxetine

Paroxetine is orally administered, inter alia, for the treatment of depression, social anxiety disorders, obsessive compulsive disorder, panic disorder, generalized anxiety disorder and posttraumatic stress disorder.

U.S. Pat. Nos. 4,902,801 and 5,258,517, and EP 223,334 A1, each of which is incorporated herein in its entirety, disclose preparation of paroxetine by condensation of cinnamate of formula 1 with alkyl amidomalonate of formula 2 to produce imide of formula 3, followed by subsequent transformations, as shown in Scheme I below:

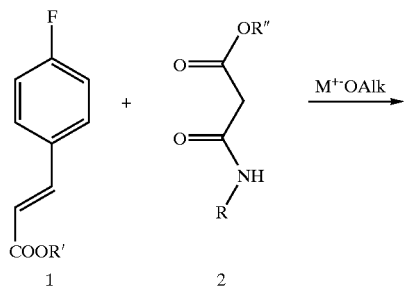

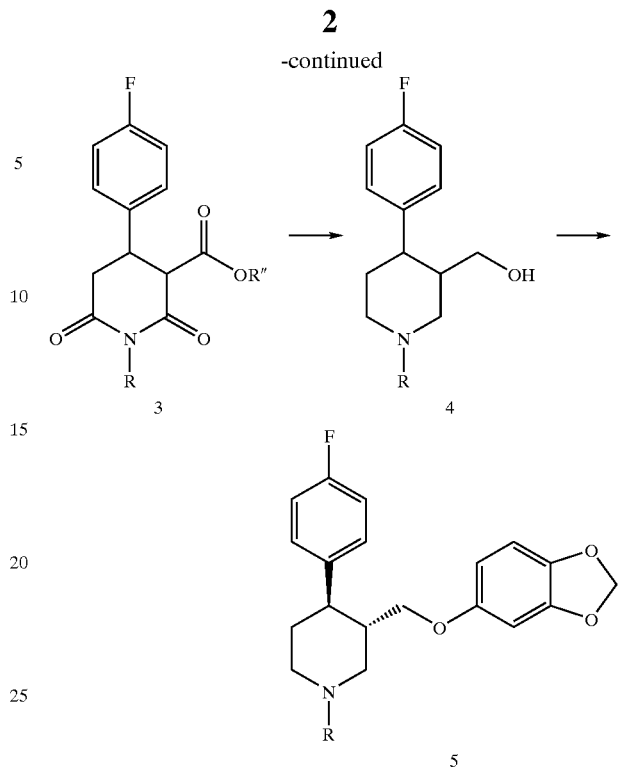

The '801 and the '517 patents and EP 223,334 A1 disclose catalyzing the reaction of the cinnamate and the amidomalonate with an alkali metal alkoxide, such as potassium tert-butoxide.

One problem with the synthesis of paroxetine is the defluorination of the intermediates. For example, U.S. Pat. No. 6,326,496, discloses a method for preparing paroxetine to minimize the amount of defluorination.

Defluorination is particularly problematic when the condensation of the cinnamate and the alkyl amidomalonate occurs in the presence of a metal alkoxide as disclosed in the '517 and '801 patents. The reaction can produce the undesired impurity of formula 6, wherein the alkoxy group is substituted for the fluorine substituent.

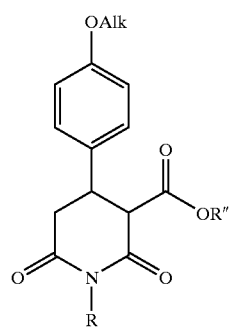

When the compound of formula 3 is subsequently reduced to obtain the compound of formula 4, the impurity of formula 6 is also reduced in a similar fashion. The reduction of the impurity leads to the intermediate of formula 4, i.e. 1-methyl-3-hydroxymethyl-4-(4'-fluorophenyl)piperidine ("PMA"), being contaminated with the corresponding impurity of formula 7 (shown below), and a final paroxetine product contaminated with the corresponding alkoxy impurity.

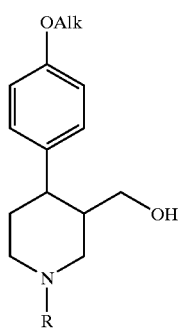

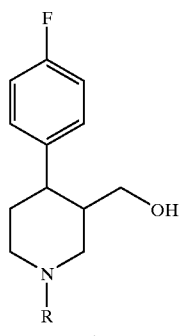

Thus, at each stage of the process leading to paroxetine, an alkoxy impurity corresponding to the desired intermediate, or to paroxetine, may be present. The alkoxy impurities can not be effectively separated from paroxetine or its intermediates by traditional techniques such as recrystallization. It is believed that the polarity and the structure of the alkoxy impurities is too similar to those of paroxetine and its intermediates to allow for effective separation. Thus, there is a need in the art to prepare paroxetine substantially free of alkoxy impurities.

SUMMARY OF THE INVENTION

In one aspect, the present invention is directed to a process for preparing paroxetine substantially free of alkoxy impurities. The alkoxy group is removed by reacting the alkoxy impurity with an ether cleaving agent followed by separation to obtain the desired intermediate or paroxetine substantially free of the corresponding alkoxy impurity. A reaction scheme representing a preferred embodiment of the present invention is provided below:

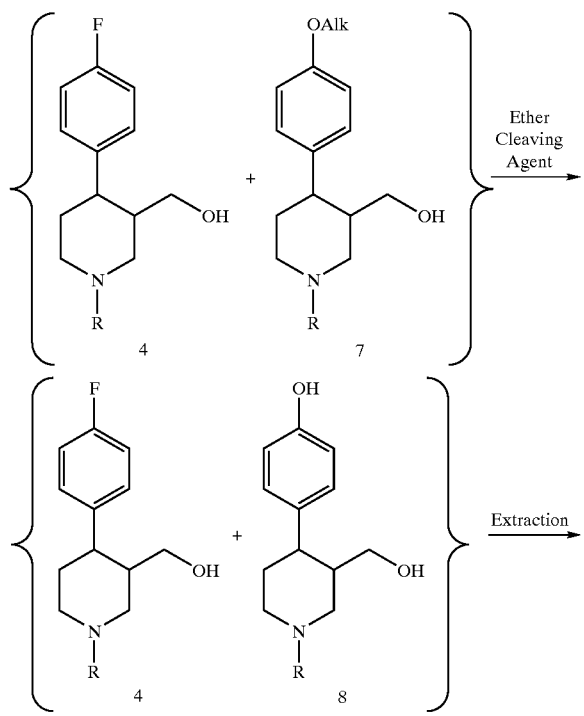

In this embodiment, removal of the alkoxy group results in the corresponding phenol of formula 8. The desired product (PMA) can be effectively separated from the corresponding phenol, preferably by extraction, resulting in PMA substantially free of the corresponding alkoxy impurity. Among preferred non-limiting examples of ether cleaving agents include hydrogen halides, such as HI and HBr. Other ether cleaving agents include, e.g., LiI, BBr$_3$ (Lewis acid), AlCl$_3$, AlBr$_3$, HBr/HOAc, trimethylsilyliodide, EtS$^-$Na$^+$, MeMgI, (Grignard reagent) and CF$_3$CO$_2$H.

The ether cleaving reaction can be conducted in water, an organic solvent or mixtures thereof. Suitable organic solvents include, for example, aromatic hydrocarbons such as toluene and xylene. Dimethylformamide ("DMF") can be used as a solvent where the ether cleaving agent is, e.g., EtS$^-$Na$^+$ or the combination of acetic acid and HBr.

Suitable extraction solvents for separating the desired intermediate, e.g., PMA or paroxetine from the corresponding phenolic compound include, e.g., ethers, ketones, esters and chlorinated hydrocarbons. Specific examples of such solvents include methylene chloride, ethyl acetate, tert-butyl methyl ether and chloroform.

The result of the process is an intermediate of formula 4 (PMA) that is substantially free of alkoxy impurities. The intermediate can then be converted to paroxetine base that is also substantially free of alkoxy impurities. The paroxetine base so prepared can be converted into an acid addition salt, preferably paroxetine hydrochloride, either as a hemihydrate or an anhydrate. Other polymorphs and solvates of paroxetine salts, such as paroxetine hydrochloride isopropanolate, can also be prepared.

The present invention is further directed to pharmaceutical compositions of paroxetine, or pharmaceutically acceptable salts thereof, such as the hydrochloride salt, substantially free of alkoxy impurities and methods of administering paroxetine or pharmaceutically acceptable salts thereof, substantially free of alkoxy impurities, for blocking the re-uptake of serotonin and other therapeutic indications as are known in the art for paroxetine and its pharmaceutically acceptable acid addition salts.

DETAILED DESCRIPTION OF THE INVENTION

Figure 1:
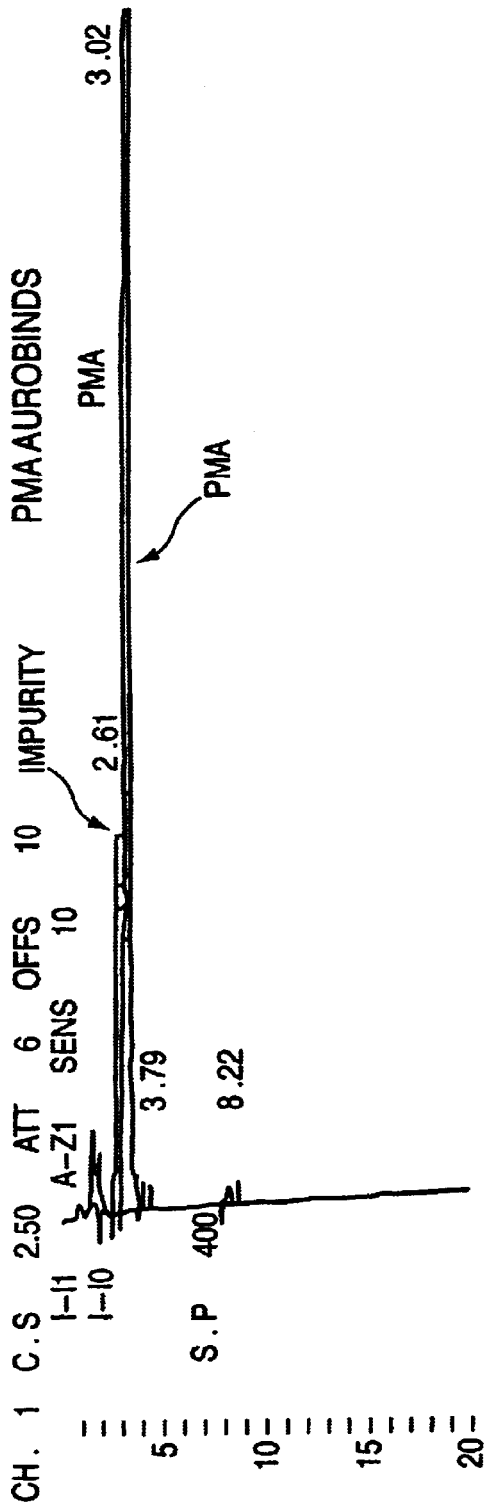
FIG. 1 is an HPLC chromatogram of commercially available PMA showing the level of the alkoxy impurity represented by peak No. 1 with an area percentage of 2.574%. PMA is shown as Peak No. 2.
Figure 2:
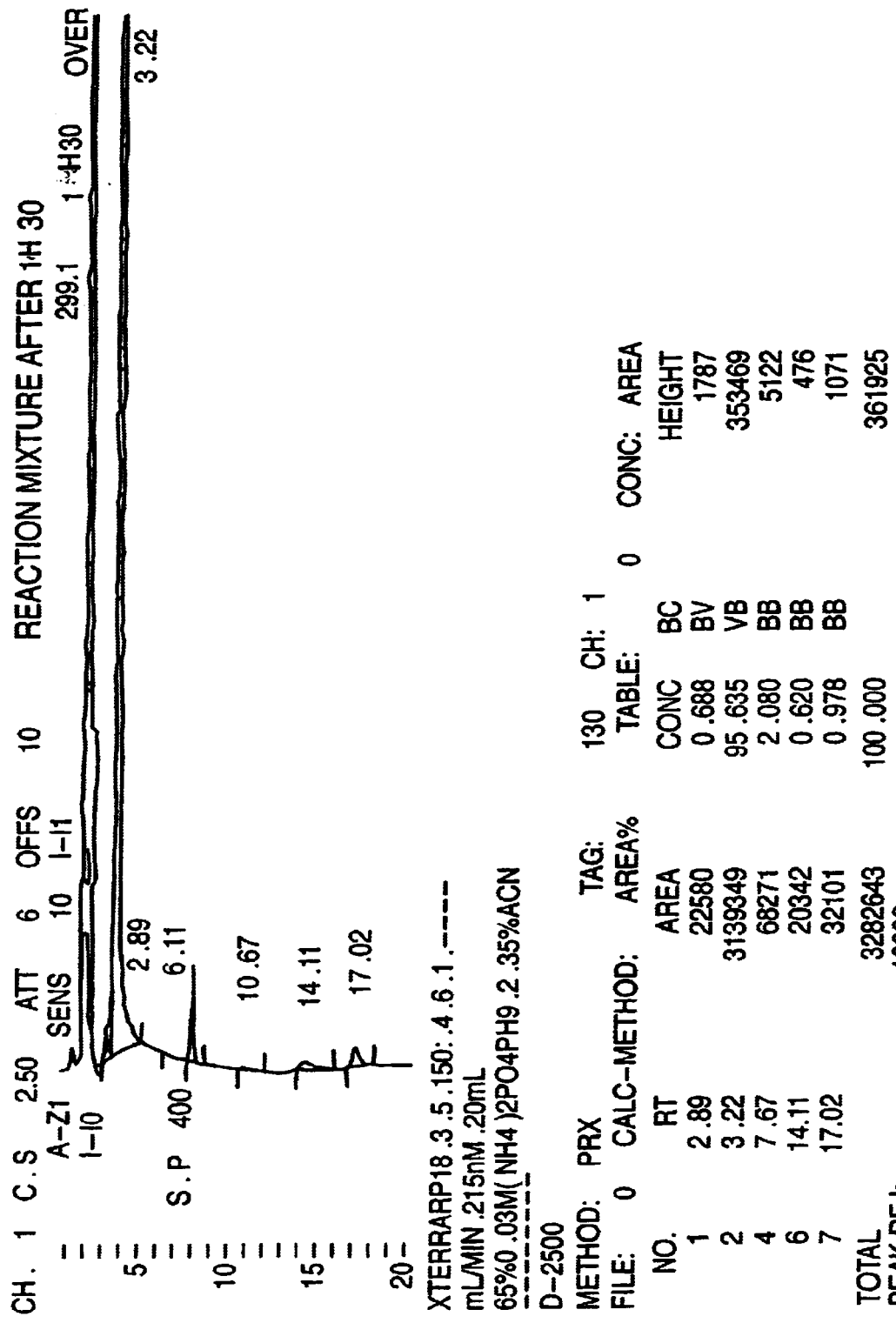
FIG. 2 is an HPLC chromatogram of the reaction mixture containing PMA after being heated for 1.5 hours at reflux as described in the Example. The level of the alkoxy impurity represented by Peak No. 1 has an area percentage of 0.688%.
Figure 3:
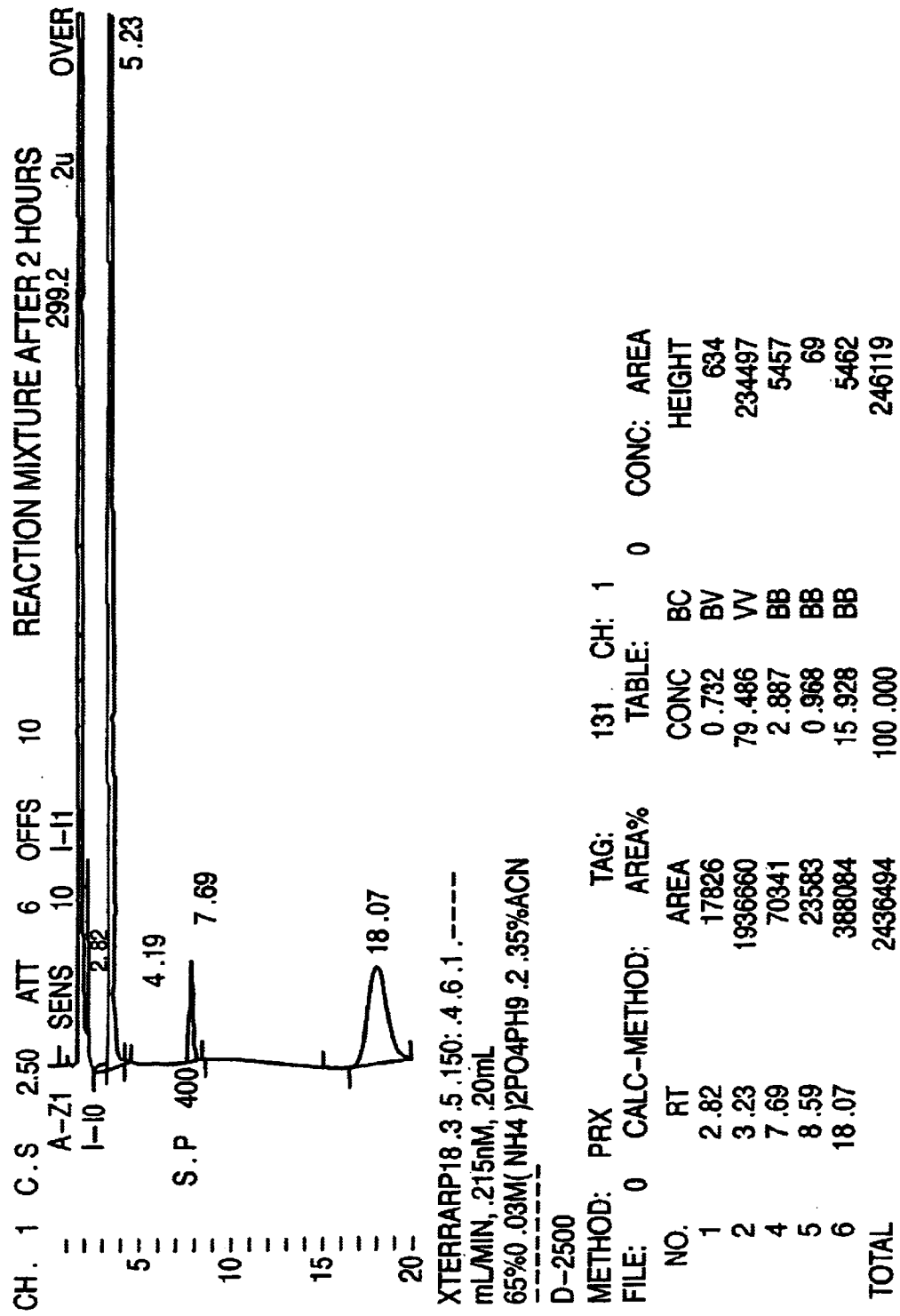
FIG. 3 is an HPLC chromatogram of the same reaction mixture after being heated for 2 hours. The level of the alkoxy impurity is not detectable by HPLC, as evidenced by the absence of Peak No. 1. (The peak in the chromatogram having a retention time of 2.82 minutes corresponds in the spectra to the small bump seen near the peak; it is not the integration of an impurity but more probably an artefact).
Figure 4:
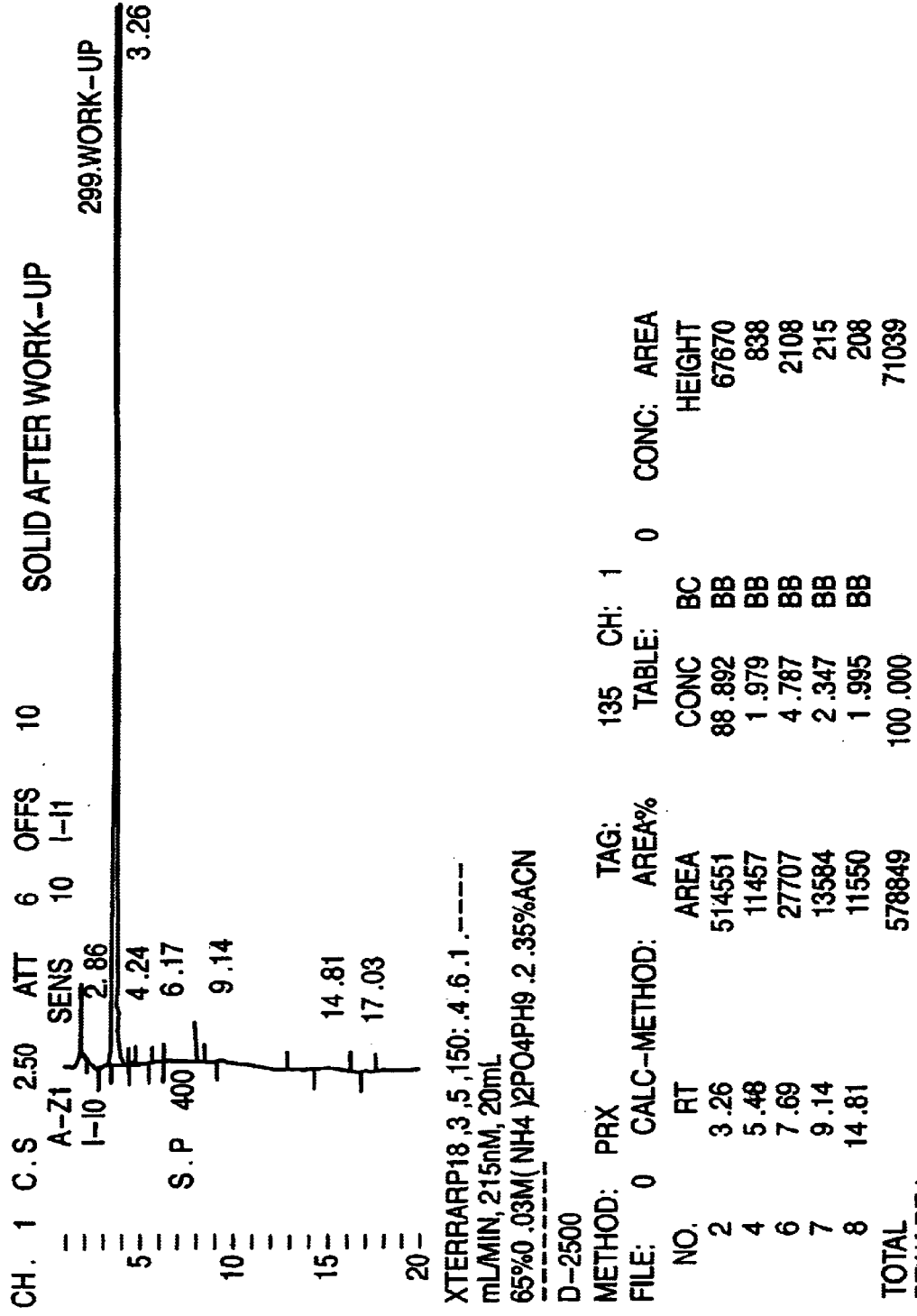
FIG. 4 is an HPLC chromatogram of PMA substantially free of the corresponding alkoxy impurity, after crystallization and work-up of the PMA. The level of the alkoxy impurity is not detectable by HPLC, as evidenced by the absence of Peak No. 1.

In one aspect, the present invention is directed to a process for preparing paroxetine substantially free of alkoxy impurities. Without being bound by theory, it is believed that removal of the alkoxy group from the alkoxy impurity to obtain the corresponding phenol changes the physical characteristics of the impurity to a degree that enables its effective separation from the desired compound. Separation can be carried out by methods generally known in the art, such as chromatography or, preferably, solvent extraction.

As used herein, the term "substantially free of", as used in reference to the level of the alkoxy impurity, refers to the area percentage of the peak representing the alkoxy impurity in an HPLC chromatogram obtained from a mixture comprising the desired compound and the alkoxy impurity.

As used herein, the term "alkoxy impurity" refers to paroxetine or an intermediate in the synthesis of paroxetine, such as PMA, in which the fluorine atom at the 4-position of the phenyl group is replaced with an alkoxy group.

A preferred embodiment of the process of the present invention is illustrated by the following reaction scheme:

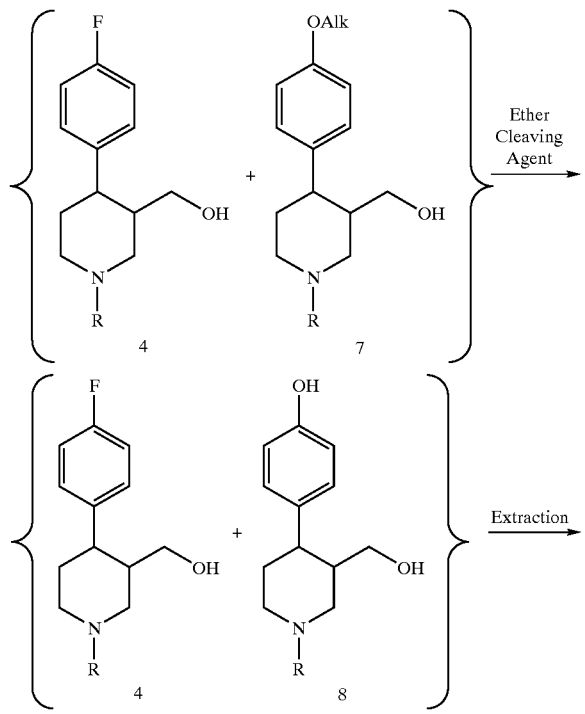

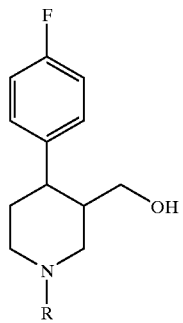

Upon reaction of the alkoxy impurity of formula 7 with an ether cleaving agent, the corresponding phenolic compound of formula 8 is formed.

The alkoxy impurity of formula 7 arises upon the reduction of the compound of

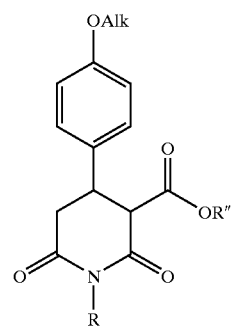

formula 3 contaminated with the alkoxy impurity of formula 6, which is similarly reduced: One of skill in the art can appreciate that the general order of reduction and removal of the alkoxy group does not necessarily affect the results. Thus, it is possible that the alkoxy group be removed from a compound of formula 6 followed by reduction to yield the corresponding phenol of formula 8.

As used herein, "Alk" refers to a $C_1$ to a $C_7$ straight or branched, substituted or unsubstituted, saturated or unsaturated alkyl group. Preferably, "Alk" is a completely saturated alkyl group. Specific examples of such alkyl groups include methyl, ethyl, propyl, isopropyl, and butyl groups such as t-butyl and isobutyl.

As used herein, R is a suitable amine protecting group that is inert, resistant to reduction by a metal hydride, and stable enough to protect the amine of the piperidine ring at all times. Examples of such amine protecting groups are disclosed in U.S. Pat. No. 6,326,496, which is incorporated herein in its entirety. Preferably, R is a $C_1$ to a $C_7$ lower alkyl group, and most preferably, a methyl group.

As used herein, R" is a straight or branched, substituted or unsubstituted, saturated or unsaturated alkyl group as disclosed in the '801 patent. Preferably, R" is a $C_1$ to a $C_7$ alkyl group. Completely saturated $C_1$ to $C_4$ alkyl groups are preferred.

OR' in the cinnamate of formula 1 refers to a suitable leaving group as disclosed in the '801 patent. Preferably, R' is a $C_1$ to a $C_7$ alkyl group. Completely saturated $C_1$ to $C_4$ alkyl groups are preferred.

The paroxetine intermediate of formula 3 can be reduced by methods known in the art, for example, using a metal hydride, such as lithium aluminum hydride or aluminum hydride, in an inert solvent, such as toluene or tetrahydrofuran. However, upon reduction of the paroxetine intermediate of formula 3 to give PMA, the impurity of formula 6 is reduced as well, resulting in the contamination of the PMA by the impurity of formula 7. To separate the impurity of formula 7 from PMA, the alkoxy group is cleaved from the impurity. In accordance with present invention, the alkoxy impurity of formula 7 is reacted with an ether cleaving agent. Techniques for cleaving ethers are generally well known in the art and can be adapted to remove the alkoxy group from the alkoxy impurity in accordance with the present invention.

One method for cleaving ethers is by protonation in acidic conditions, followed by nucleophilic substitution. This is a preferred method for cleaving the alkoxy group from the alkoxy impurity in accordance with the present invention. A preferred protic acid is a hydrogen halide. Among preferred hydrogen halides are hydrogen iodide ("HI") and hydrogen bromide ("HBr"). Other ether cleaving agents include, e.g., LiI, $BBr_3$ (Lewis acid), $AlCl_3$, $AlBr_3$, HBr/HOAc, trimethylsilyliodide, $EtS^-Na^+$, MeMgI (Grignard reagent) and $CF_3CO_2H$.

Hydrogen halides are preferred ether cleavage agents, particularly where the alkoxy group is unbranched, such as in ethoxy or methoxy, and the reaction proceeds via an $S_N2$ mechanism. Such a strong nucleophile can be an iodide ion present as a result of dissociation of hydrogen iodide. However, when the alkoxy group is a branched group, such as a tert-butyl group, a weaker nucleophile, such as provided by $CF_3CO_2H$ may be sufficient. In such a case, the reaction proceeds via an $S_N1$ mechanism.

The ether cleaving reaction can be carried out in water, a suitable organic solvent, or mixtures thereof. Examples of suitable organic solvents are aromatic hydrocarbons, such as toluene and xylene, with toluene being preferred. Dimethylformamide ("DMF") can be used as a solvent where the ether cleaving agent is, e.g., $EtS^-Na^+$ or the combination of acetic acid and HBr.

The ether cleavage reaction can be conducted under conditions generally known to the person of ordinary skill in the art. Such conditions can, of course, be modified to obtain optimal results, especially in light of the fact that ethers are generally stable and resistant to cleavage. For example, when using a hydrogen halide, high concentrations of HBr and/or HI coupled with high temperatures may be used to accelerate the process. The concentration of hydrogen halides used is preferably from about 1 to about 20 equivalent, more preferably about 10 equivalents. The mixture is heated from about 30° C. to about reflux, with reflux temperature being preferred.

The reaction can be monitored for completion, such as by testing a sample of the reaction mixture at various times with high pressure liquid chromatography (HPLC). Upon completion of the reaction, the pH of reaction mixture can be adjusted with a base. The reaction is determined to be substantially complete when the peak representing the alkoxy impurity in an HPLC chromatogram of the reaction mixture has an area percentage of less than about 0.5%. It is particularly advantageous to increase the pH of the reaction mixture to increase the solubility of the corresponding phenol in the aqueous phase upon extraction with a suitable solvent. Bases known in the art such as alkali or alkaline earth metal oxides or hydroxides are useful for this purpose. Examples of such bases include sodium and potassium hydroxide. Preferably, the pH of the reaction mixture is adjusted to from about 9 to about 12, more preferably from about 10 to about 12, to facilitate the subsequent separation of the desired intermediate or paroxetine base from the corresponding phenolic compound, i.e., the product of the ether cleavage.

The cleavage of the ether of formula 7 results in the corresponding phenol of formula 8. The corresponding phenol can then be separated from the desired intermediate of formula 4, i.e., PMA, by extraction.

The organic solvent used for extraction is preferably one that selectively extracts the PMA from the reaction medium while having minimal solubility for the phenolic compound of formula 7. General examples of such solvents include ethers, ketones, esters and chlorinated hydrocarbons. Specific examples of such solvents include methylene chloride, ethyl acetate, chloroform and methyl t-butyl ether (MTBE). Methylene chloride is preferred.

After extraction, the aqueous phase, containing the corresponding phenol produced from the ether cleavage reaction, is discarded while the organic phase containing PMA substantially free of alkoxy impurity, is kept for further purification and/or conversion to paroxetine or a pharmaceutically acceptable salt of paroxetine. The organic phase is preferably concentrated and, optionally, dried with a drying agent, such as sodium sulfate. The organic phase can be concentrated by, e.g., evaporation under ambient or reduced pressure, with or without the use of a drying agent. If a drying agent is used, the concentrated organic phase is subsequently filtered to remove the agent. The concentrated oily organic phase can then be seeded to induce crystallization of the PMA.

To further purify the crystals, they can be slurried in an organic solvent, followed by separation, such as by filtration. Suitable solvents include $C_5$ to $C_{12}$ saturated hydrocarbons and aromatic hydrocarbons. Specific examples of solvents include heptane, hexane, cyclohexane, xylene, toluene and benzene.

The crystals are then separated from the solvent. Techniques known in the art, such as filtration, can be used to separate the crystals. After separation, the crystals are dried. To accelerate the drying, the temperature can be raised or the pressure reduced. Drying may be conducted by conventional methods, such as oven drying at a temperature of from about 40° C. to about 60° C., with about 50° C. being preferred. The result of this process is a slightly yellow powder of PMA, substantially free of alkoxy impurities. PMA substantially free of alkoxy impurities is an important product in accordance with the present invention as it is a useful intermediate in the synthesis of paroxetine free of alkoxy impurities.

By "substantially free of alkoxy impurities" is meant that any of the desired compounds including PMA, paroxetine base, or pharmaceutically acceptable salts of paroxetine such as paroxetine HCl (in any of the various polymorphic or solvate forms) prepared in accordance with the present invention contains less than about 0.5%, more preferably less than about 0.1%, and even more preferably, less than about 0.05% of the corresponding alkoxy impurity as characterized by HPLC and NMR. In comparison, commercially available PMA contains a level of the corresponding alkoxy impurity of formula 7 of about 3%. The percentages herein refer to area percentages of the peak representing the alkoxy impurity in an HPLC chromatogram obtained from a mixture comprising the desired compound and the alkoxy impurity.

If the ether cleavage reaction is carried out in a non-aqueous medium, then a less polar solvent is used to extract the desired intermediate substantially free of alkoxy impurities. One skilled in the art will readily appreciate that an optimal extraction solvent is one having high affinity for the desired paroxetine intermediate and little or no affinity for the corresponding phenol resulting from the ether cleavage reaction.

One of skill in the art can appreciate that, after cleavage of the ether, separation techniques other than solvent extraction can be used to separate the corresponding phenol from the desired paroxetine intermediate such as PMA. For example, HPLC, thin layer or gas chromatography can be used to separate the corresponding phenol from the paroxetine intermediate. The stationary phase can have a higher affinity for the more polar phenol compound while the mobile phase can have a higher affinity for the less polar paroxetine intermediate, resulting in effective separation of the compounds. After separation, the resulting material can be slurried and separated as described above.

The resulting product, PMA that is substantially free of the corresponding alkoxy intermediate, can be converted to paroxetine in a manner generally known in the art as disclosed, e.g., in U.S. Pat. Nos. 4,902,801 and 5,258,517, and EP 223,334 B. In one embodiment, the hydroxyl group of PMA is first converted to a haloalkyl group or a sulfonate ester group by methods well known in the art, as disclosed, for example, in U.S. Pat. Nos. 5,258,517 and 4,585,777, each of which is incorporated herein in its entirety. For example, phosphorous tribromide ($PBr_3$), phosphorous trichloride ($PCl_3$) and thionyl chloride ($SOCl_2$) can be used to convert the alcohol into an alkyl halide. In another embodiment, a sulfonyl compound can be used to convert the intermediate into a sulfonate ester. Specific examples of such sulfonyl compounds include sulfonyl chlorides, such as trifluoromethanesulfonyl chloride, p-toluenesulfonyl chloride (tosyl chloride), methanesulfonyl chloride (mesyl chloride) and benzenesulfonyl chloride (besyl chloride). Pyridine can be used as a solvent to neutralize any hydrochloric acid formed. The resulting alkyl halide or sulfonyl ester can then be converted to paroxetine.

For example, an alkyl halide, such as 4-(4-fluorophenyl)-3-chloromethyl-N-methyl-piperidine (CIPMA) of formula:

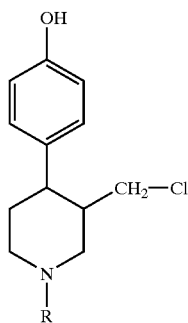

is reacted with 3,4-methylenedioxyphenol ("sesamol") of formula:

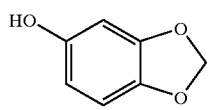

in a suitable basic solvent, such as a methanolic solution of sodium, to obtain N-methylparoxetine, followed by alkaline hydrolysis. This process is disclosed for example in U.S. Pat. Nos. 4,007,196 and 4,585,777, each of which is incorporated herein in its entirety.

The ether cleavage reaction is preferably carried out before reaction of CIPMA with sesamol. This order is preferred because N-methylparoxetine and paroxetine base each has a methylenedioxy (acetal) group susceptible to cleavage during the ether cleavage reaction used to remove the alkoxy group from the alkoxy impurity.

The paroxetine base prepared by the present process, which is substantially free of the alkoxy impurities, can be converted to an acid addition salt, preferably a pharmaceutically acceptable acid addition salt such as the hydrochloride salt. The paroxetine or any acid addition salt thereof can be made in any of the known polymorphic forms such as solvates, hemihydrates and anhydrates. A preferred pharmaceutically acceptable acid addition salt is paroxetine HCl, which can be made in any of the various polymorphic forms known in the art. Among the presently preferred polymorphic/pseudopolymorphic forms of paroxetine HCl included are crystalline paroxetine hydrochloride hemihydrate of U.S. Pat. No. 4,721,723, and any of the paroxetine hydrochloride anhydrate and solvate forms, particularly the isopropanolate, of U.S. Pat. No. 6,080,759. The term "anhydrate" as used herein refers to a crystalline structure that is substantially free of bound solvents. By "substantially free of bound solvents" is meant containing less than about 5% w/w, preferably less than about 2% w/w bound solvent such as isopropanol. The term "bound solvent" does not refer solvent that is not part of the crystalline structure, i.e., residual solvent not stoichiometrically associated with the crystalline structure.

Paroxetine base in solution can be converted to paroxetine HCl, for example, by contacting a solution or slurry of paroxetine base with aqueous or gaseous HCl, followed by crystallization in an appropriate solvent to obtain the desired polymorphic form. When the desired polymorphic form is the hemihydrate, it is preferable to contact the solution of paroxetine base with aqueous HCl followed by crystallization as generally disclosed in U.S. Pat. No. 4,721,723. When the desired polymorphic form is anhydrous paroxetine HCl or the paroxetine HCl isopropanolate, a solvent solution of paroxetine base is preferably contacted with dry hydrogen chloride gas or a solvent substantially free of water, wherein the solvent has hydrogen chloride gas dissolved therein. U.S. Pat. No. 6,080,759 discloses methods for the preparation of anhydrous forms of paroxetine HCl. The solvents used to form the anhydrates are substantially free of water, meaning that there is insufficient water present at the time of crystallization to effect conversion to a hydrated form of paroxetine HCl such as the hemihydrate. A solvent substantially free of water can be obtained by drying the solvent with a conventional drying agent such as a molecular sieve. Anhydrous solvents can also be purchased commercially.

Crude paroxetine hydrochloride hemihydrate can be formed, for example, from a toluenic solution of paroxetine base by contacting the solution of paroxetine base with aqueous HCl followed by crystallization in an appropriate solvent, as generally disclosed in U.S. Pat. No. 4,721,723. Crystalline paroxetine hydrochloride hemihydrate can then be prepared by recrystallization of the crude paroxetine hydrochloride hemihydrate in a suitable solvent. Suitable solvents include, for example, lower alkanols, such as methanol and ethanol, ketones, such as acetone, esters, such as ethyl acetate and mixtures of any of the foregoing, such as methanol/acetone.

Anhydrous forms of paroxetine hydrochloride can be formed by the methods generally disclosed in U.S. Pat. No. 6,080,759. The anhydrous forms are preferably substantially free of bound solvents, as discussed hereinabove. Anhydrous paroxetine hydrochloride, e.g., can be prepared by contacting, in a dry $N_2$ environment, a solution of paroxetine base in an organic solvent, such as isopropanol, with dry hydrogen chloride gas. Alternatively, the solution of paroxetine base in an organic solvent can be contacted with a solvent substantially free of water wherein the solvent has dry hydrogen chloride gas dissolved therein. The reaction mixture is heated to ensure complete dissolution of the paroxetine hydrochloride. Seed crystals of paroxetine HCl anhydrate can be added to improve the crystallization process.

As disclosed in U.S. Pat. No. 6,080,759, anhydrous forms of paroxetine HCl substantially free of bound solvent can also be prepared from paroxetine HCl hemihydrate by dissolving the hemihydrate in an appropriate solvent substantially free of water which forms an azeotrope with water. Suitably, solvent is removed by distillation and fresh solvent is added until all of the water is removed.

The anhydrous forms substantially free of bound solvent can also be made by crystallizing paroxetine hydrochloride in an organic solvent or a mixture of solvents, which form a solvate with the paroxetine hydrochloride, and displacing the solvated solvent or solvents from the paroxetine hydrochloride solvate using a displacing agent. Preferably, gaseous or liquid water can be used as the displacing agent. It is important that the paroxetine hydrochloride solvate is contacted with enough water and for a sufficient amount of time to displace the solvent, but not enough time to cause conversion to the hydrochloride hemihydrate.

Paroxetine HCl can also be prepared in various solvate forms, as disclosed in U.S. Pat. No. 6,080,759, incorporated herein in its entirety. Among the preferred solvate forms is paroxetine hydrochloride isopropanolate disclosed for example in Examples 1–3 of the '759 patent. Paroxetine HCl isopropanolate can be formed by displacing water from paroxetine HCl hemihydrate in, for example, a mixture of toluene and isopropanol followed by crystallization. Paroxetine HCl isopropanolate can also be formed by contacting a solution of paroxetine base in isopropanol with dry hydrogen chloride gas followed by crystallization. The isopropanolate can also be formed by contacting a solution of paroxetine base in dry isopropanol with a solution of dry hydrogen chloride gas in dry isopropanol followed by crystallization. Solvates other than the isopropanolate can be made by similar methods, as disclosed in the '759 patent. Among such solvates are those derived from solvents, such as alcohols (other than isopropanol, such as 1-propanol and ethanol); organic acids, such as acetic acid; organic bases, such as pyridine; nitrites, such as acetonitrile; ketones, such as acetone and butanone; ethers, such as tetrahydrofuran; chlorinated hydrocarbons, such as chloroform; and hydrocarbons, such as toluene. These solvates can be used to form the anhydrous forms substantially free of bound solvent by either displacing the solvent, as described above, or by removing the solvent by conventional techniques, such as vacuum oven drying.

The term "paroxetine hydrochloride" as used in the present invention includes all of the above and other polymorphic and solvate forms.

In accordance with the present invention, the highly pure forms of paroxetine or a pharmaceutically acceptable salt thereof such as the hydrochloride salt, i.e., those forms substantially free of the alkoxy impurities, prepared by the methods disclosed herein can be formulated as pharmaceutical compositions that, upon administration, are are particularly useful for inhibiting the re-uptake of serotonin. Such compositions can comprise any of the various polymorphic and/or solvate forms of paroxetine or pharmaceutically acceptable salts thereof such as the hydrochloride salt with pharmaceutically acceptable carriers and/or excipients known to one of skill in the art.

For example, pharmaceutical compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with a hydrophilic or hydrophobic vehicle. For topical administration, suitable transdermal delivery systems known in the art and, for nasal delivery, suitable aerosol delivery systems known in the art may be employed.

A particularly preferred unit dosage form is a coated tablet. Such a tablet contains a pharmaceutically effective amount of paroxetine or a pharmaceutically acceptable salt thereof, such as the hydrochloride salt, in accordance with the present invention in conjunction with one or more excipients, such as a binder, filler, stabilizer, disintegrant, glidant, flavoring and coloring agents A pharmaceutically acceptable amount of a salt of paroxetine, such as the hydrochloride salt, is approximately from about 10 mg to about 200 mg of the base equivalent, as disclosed in U.S. Pat. No. 6,080,759, more preferably from about 10 mg to about 100 mg, and most preferably from about 10 mg to about 50 mg.

Paroxetine or a pharmaceutically acceptable salt thereof may also be formulated as a suspension containing, for example, a dosage of about 10 mg of the base equivalent of the pharmaceutically acceptable salt, per 5 ml of liquid. The effective dose for the suspension is about the same as that for the tablet.

Instrumentation Used

High pressure liquid chromatography is performed on XTERRA RP-18 (3.5 um; 150×4.6 mm), reverse phase column with di-ammonium hydrogen phosphatebuffer solution; acetonitrile mixture. Detected by U.V. spectroscopy at $\lambda=215$ nm.

EXAMPLE

Purification of 1-methyl-3-hydroxymethyl-4-(4'-fluorophenyl)piperidine (PMA)

PMA (30 grams—containing approximately 2.6% by HPLC area percentage of the corresponding alkoxy impurity) was added to a solution of HBr (180 ml, 48%). The reaction mixture was then heated to strong reflux for about 1.50 hours until completion of the reaction. The reaction was followed by HPLC until the area percentage of the peak representing the alkoxy impurity is less than 0.5%. The reaction mixture was then allowed to cool to 0° C., and was then basified to pH=11.5 with a solution 40% NaOH to increase the solubility of the corresponding phenol in the aqueous phase. Methylene chloride (150 ml) was then added, and the aqueous phase was extracted 3 times with methylene chloride (3×150 ml). The organic phase was then dried on sodium sulfate, filtrated and evaporated under reduced pressure, leaving about 15 g of methylene chloride. The oily mixture was then seeded with PMA crystal and after 1 hour the entire reaction mixture was crystallized. Heptane (100 ml) was added to the crystals and the mixture was slurried for 15 minutes. Then, the slightly yellow slurry was filtered and dried for 4 hours in an oven at 50° C. to obtain 25.67 g (85.5%) of a light yellow powder substantially free of the corresponding alkoxy impurity.

The following tables disclose the characterization of each peak from the Figures, and numerically correspond to the Figures.

TABLE 1

| No. | RT | Area | Concentration | BC | Height |
|---|---|---|---|---|---|
| 1 | 2.61 | 117016 | 2.574 | BV | 17969 |
| 2 | 3.02 | 4416762 | 97.168 | VV | 606004 |
| 4 | 8.22 | 11732 | 0.258 | BB | 863 |
| TOTAL | | 4545510 | 100.000 | | 624836 |

TABLE 2

| No. | RT | Area | Concentration | BC | Height |
|---|---|---|---|---|---|
| 1 | 2.89 | 22580 | 0.688 | BV | 1787 |
| 2 | 3.22 | 3139349 | 95.635 | VB | 353469 |
| 4 | 7.67 | 68271 | 2.080 | BB | 5122 |
| 6 | 14.11 | 20342 | 0.620 | BB | 476 |
| 7 | 17.02 | 32101 | 0.978 | BB | 1071 |
| TOTAL | | 3282643 | 100.000 | | 361925 |

TABLE 3

| No. | RT | Area | Concentration | BC | Height |
|---|---|---|---|---|---|
| 1 | 2.82 | 17826 | 0.732 | BV | 634 |
| 2 | 3.23 | 1936660 | 79.486 | VV | 234497 |
| 4 | 7.69 | 70341 | 2.887 | BB | 5457 |
| 5 | 8.59 | 23583 | 0.968 | BB | 69 |
| 6 | 18.07 | 388084 | 15.928 | BB | 5462 |
| TOTAL | | 2436494 | 100.000 | | 246119 |

TABLE 4

| No. | RT | Area | Concentration | BC | Height |
|---|---|---|---|---|---|
| 2 | 3.26 | 514551 | 88.892 | BB | 67670 |
| 4 | 5.48 | 11457 | 1.979 | BB | 838 |
| 6 | 7.69 | 27707 | 4.787 | BB | 2108 |
| 7 | 9.14 | 13584 | 2.347 | BB | 215 |
| 8 | 14.81 | 11550 | 1.995 | BB | 208 |
| TOTAL | | 5788490 | 100.000 | | 71039 |

Having thus described the invention with reference to particular preferred embodiments and illustrative Example, those in the art will readily appreciate modifications to the invention as described and illustrated that do not depart from the spirit and scope of the invention as disclosed in the specification. The Example is included to aid in understanding the invention but is not to be construed as limiting the scope of the present invention as defined by the claims appended hereto. Descriptions of conventional methods that do not aid in understanding the present invention have not been included. Such methods are well known to those of ordinary skill in the art and are described in numerous publications. All references mentioned herein are incorporated in their entirety.

What is claimed is:

1. A process for separating a compound of formula:

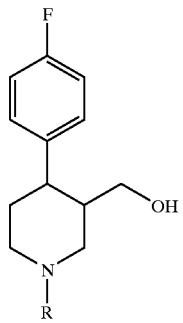

from a mixture of a compound of formula 4 and a compound of formula 7

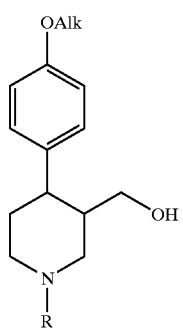

comprising converting in a suitable solvent the compound of formula 7 in the mixture to a compound of formula:

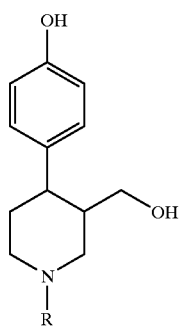

and separating the compound of formula 4 from the compound of formula 8, wherein R is a suitable amine protecting group, and Alk is a $C_1$ to a $C_7$ alkyl group.

2. The process of claim 1, further comprising converting the compound of formula 4 to paroxetine base.

3. The process of claim 2, further comprising converting the paroxetine base to paroxetine hydrochloride.

4. The process of claim 1, wherein the compound of formula 7 is converted to the compound of formula 8 by contacting the mixture with an ether cleaving agent.

5. The process of claim 4, wherein the ether cleaving agent is selected from the group consisting of a hydrogen halide, a Lewis acid and a Grignard reagent.

6. The process of claim 4, wherein the ether cleaving agent is selected from the group consisting of HBr, HI, LiI, BBr₃, AlCl₃, AlBr₃, HBr/HOAc, trimethylsilyliodide, EtS⁻Na⁺, MeMgI and CF₃CO₂H.

7. The process of claim 1, further comprising separating the compound of formula 4 from the compound of formula 8 by extraction.

8. The process of claim 7, wherein said separating comprises the steps of:
 a) contacting a mixture of the compound of formula 4 and the compound of formula 8 with a first organic solvent to obtain an organic phase and an aqueous phase;
 b) separating the organic phase containing the compound of formula 4 from the aqueous phase containing the compound of formula 8;
 c) crystallizing the compound of formula 4 from the organic phase to obtain crystals;
 d) slurrying the crystals in a second organic solvent; and
 e) separating the crystals from the second organic solvent.

9. The process of claim 1, wherein the mixture is prepared by reacting in a suitable solvent a compound of formula:

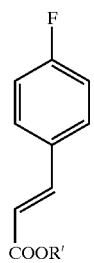

1 with a compound of formula:

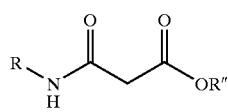

2 in the presence of an alkoxide catalyst followed by reduction, wherein R is a suitable amine protecting group, and R=, R@ and Alk represent the same or different $C_1$ to $C_7$ alkyl groups.

10. A process for purifying 1-methyl-3-hydroxymethyl-4-(4'-fluorophenyl)-piperidine (PMA) comprising reacting a mixture of PMA and its corresponding alkoxy impurity with an ether cleaving agent to obtain the corresponding phenol, followed by separating the corresponding phenol from PMA, thereby obtaining PMA substantially free of its corresponding alkoxy impurity.

11. The process of claim 10, further comprising converting PMA substantially free of alkoxy impurity to paroxetine base substantially free of alkoxy impurity.

12. The process of claim 11, further comprising converting the paroxetine base substantially free of alkoxy impurity to paroxetine hydrochloride substantially free of alkoxy impurity.

13. The process of claim 10, wherein the ether clearing agent is selected from the group consisting of a hydrogen halide, a Lewis acid and a Grignard reagent.

14. The process of claim 10, wherein the ether cleaving agent is selected from the group consisting of HBr, HI, LiI, BBr₃, AlCl₃, AlBr₃, HBr/HOAc, trimethylsilyliodide, EtS⁻Na⁺, MeMgI, CF₃CO₂H.

15. The process of claim 10, comprising separating the PMA from the corresponding phenol by extraction.

16. The process of claim 15, wherein said separating comprises the steps of:
 a) contacting a mixture of the PMA and its corresponding phenol with a first organic solvent to obtain an organic phase and an aqueous phase;
 b) separating the organic phase containing PMA from the aqueous phase containing the corresponding phenol;
 c) crystallizing PMA from the organic phase to obtain crystals;
 d) slurrying the crystals in a second organic solvent: and
 e) separating the crystals from the second organic solvent.

17. A process for preparing paroxetine hydrochloride comprising the steps of separating a compound of formula:

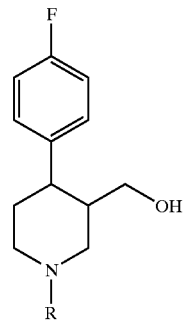

4 from a mixture of a compound of formula 4 and a compound of formula 7

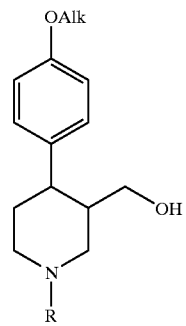

7 comprising converting in a suitable solvent the compound of formula 7 in the mixture to a compound of formula:

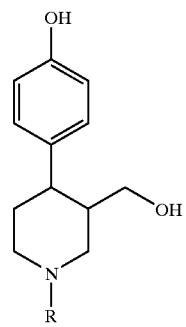

8 separating the compound of formula 4 from the compound of formula 8 and converting the compound of formula 4 to paroxetine hydrochloride, wherein R is a suitable amine protecting group, and Alk is a $C_1$ to $C_7$ alkyl group.

* * * * *